United States Patent
Pang et al.

(10) Patent No.: US 11,321,837 B2
(45) Date of Patent: May 3, 2022

(54) FIBER IMAGING APPARATUS, METHODS, AND APPLICATIONS

(71) Applicant: University of Central Florida Research Foundation, Inc., Orlando, FL (US)

(72) Inventors: Shuo Pang, Oviedo, FL (US); Yangyang Sun, Orlando, FL (US); Jian Zhao, Orlando, FL (US); Axel Schulzgen, Winter Park, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 16/898,182

(22) Filed: Jun. 10, 2020

(65) Prior Publication Data
US 2020/0394791 A1    Dec. 17, 2020

Related U.S. Application Data

(60) Provisional application No. 62/860,484, filed on Jun. 12, 2019.

(51) Int. Cl.
*G06T 7/00* (2017.01)
*G02B 6/42* (2006.01)
(Continued)

(52) U.S. Cl.
CPC .......... *G06T 7/0012* (2013.01); *G02B 6/4203* (2013.01); *G06N 3/04* (2013.01);
(Continued)

(58) Field of Classification Search
CPC ..... G06T 7/0012; G06T 5/001; G02B 6/4203; G06N 3/04
See application file for complete search history.

(56) References Cited

U.S. PATENT DOCUMENTS 10,018,558 B2 *  7/2018  Yaman ................. G01H 9/004
10,488,297 B2 * 11/2019  Saito ..................... G01M 11/33
(Continued)

OTHER PUBLICATIONS

J. Zhao et al., "Deep-Learning-Based Imaging through Glass-Air Disordered Fiber with Transverse Anderson Localization," 2018 Conference on Lasers and Electro-Optics (CLEO), 2018, pp. 1-2. (Year: 2018).*

(Continued)

*Primary Examiner* — Utpal D Shah
(74) *Attorney, Agent, or Firm* — Klintworth & Rozenblat IP LLP

(57) ABSTRACT

A flexible, artifact-free, and lensless fiber-based imaging system for biological objects. This system combines image reconstruction by a trained deep neural network with low-loss image transmission through disordered glass-air Anderson localized optical fiber. High quality images of biological objects can be obtained using short (few centimeters) or long (more than one meter) segments of disordered fiber with and without fiber bending. The deep neural network can also be designed to perform image classification. The system provides the unique property that the training performed within a straight fiber setup can be utilized for high fidelity reconstruction/classification of images that are transported through either straight or bent fiber making retraining for different bending situations unnecessary. In addition, high quality image transport and reconstruction is demonstrated for cells that are several millimeters away from the fiber input facet eliminating the need for additional optical elements at the distal end of the fiber. This novel imaging system shows great potential for practical applications in endoscopy including studies on freely behaving subjects.

10 Claims, 9 Drawing Sheets

(51) Int. Cl.
*G06N 3/04* (2006.01)
*G06T 5/00* (2006.01)
*A61B 1/06* (2006.01)
*A61B 1/00* (2006.01)

(52) U.S. Cl.
CPC ............ *G06T 5/001* (2013.01); *A61B 1/0017* (2013.01); *A61B 1/0684* (2013.01); *G06T 2207/20081* (2013.01)

(56) References Cited

U.S. PATENT DOCUMENTS 11,113,838 B2* 9/2021 Yang .................. G06N 3/08
2021/0027154 A1* 1/2021 Zalevsky ............. G06K 9/74

OTHER PUBLICATIONS

S. Karbasi, T. Hawkins, J. Ballato, K. W. Koch, and A. Mafi, "Transverse Anderson localization in a glass optical fiber with random air-holes," in Optical Fiber Communication Conference/ National Fiber Optic Engineers Conference 2013, OSA Technical Digest (online) (Optical Society of America, 2013) (Year: 2013).*
Karbasi, Salman, et al. "Image transport through a disordered optical fibre mediated by transverse Anderson localization." Nature communications 5.1 (2014): 1-9. (Year: 2014).*
J. Zhao, Y. Sun, Z. Zhu, J. E. Antonio-Lopez, R. Amezcua Correa, S. Pang, and A. Schülzgen, "Deep Learning Imaging through Fully-Flexible Glass-Air Disordered Fiber," ACS Photonics 5, 3930 (2018).
J. Zhao, Y. Sun, H. Zhu, Z. Zhu, J. E. Antonio-Lopez, R. Amezcua-Correa, S. Pang, and A. Schülzgen, "Deep Learning Cell Imaging through Anderson Localizing Optical Fibre," Advanced Photonics 1, 066001 (2019). (published online Nov. 11, 2019).

* cited by examiner

FIBER IMAGING APPARATUS, METHODS, AND APPLICATIONS

RELATED APPLICATION DATA

The instant application claims priority to U.S. Provisional Patent Application No. 62/860,484 filed Jun. 12, 2019, the subject matter of which is incorporated herein by reference in its entirety.

GOVERNMENT FUNDING

N/A.

BACKGROUND

Non-limiting aspects and embodiments most generally pertain to the field of optical imaging; more particularly biological imaging apparatus, methods, and applications thereof; and, most particularly to a deep-learning-based optical fiber imaging apparatus, methods, and applications thereof.

Fiber-optic based imaging systems have become increasingly versatile tools in biomedical research and clinical diagnostics in recent years. Of particular importance are endoscopes that permit the imaging of cells and tissues located in regions where conventional light microscopy cannot access, enabling basic research on biological and disease processes. Many types of cells reside deeply within solid organs or in hollow tissue tracts that are beyond the imaging depth of microscopes using visible light. Fiber-based endoscopes, with diameters from several hundreds of micrometers to a few millimeters, are the only devices that can reach such locations and provide images in a minimally invasive manner. This minimally invasive nature also permits implanting such devices within live subjects for developmental imaging studies, which greatly benefit the research efforts in neuroscience and aging related degenerative disease.

In neuroscience and clinical applications, visualizations of real-time cell activity, morphology, and overall tissue architecture are crucial for fundamental research and medical diagnosis. This usually requires real-time in vivo imaging to be performed in a minimally invasive way with the ability to deeply penetrate into organs. Due to the miniature size and flexible imaging transfer capability, fiber-optic imaging systems (FOISs) have been widely applied to this domain.

Current solutions are faced with challenges regarding bulky and complex distal optics, imaging artifacts, and extreme sensitivity to perturbations. These limitations mainly originate from the optical fiber device. For example, multicore fiber bundles and multimode fibers (MMFs) are the two most widely used fibers in these systems. Systems based on fiber bundles usually require extra distal optics or mechanical actuators that limit the extent of miniaturization. In addition, the particular core patterns featured in fiber bundles result in pixelated artifacts in transported images. Typical systems using MMF rely on image reconstruction processes using the transmission matrix method to compensate for randomized phases through wavefront shaping. This kind of reconstruction process is vulnerable to perturbations. Even minor changes of temperature (e.g., a few degrees Celsius) or slight fiber movement (e.g., a few hundred micrometers) can induce mode coupling and scramble the pre-calibrated transmission matrix.

Recent burgeoning deep learning technology opens a new avenue for overcoming the physical limitation of fiber devices outlined above. Deep learning technology is a fast-developing research field that has gained great success in imaging applications and demonstrated better performance than conventional model-based methods. Instead of relying on known models and priors, the deep convolutional neural network (DCNN) directly learns the underlying physics of an imaging transmission system through a training process using a large dataset without any advanced knowledge. Especially, when it is difficult to develop an accurate physics model, this learning capability demonstrates its superiority over model-based methods. The trained DCNN is a precise approximation of the mapping function between the measured imaging data and the input imaging data. Well designed and trained DCNNs can be used to predict input images even if the particular type of images is not included in the set of training data. The prediction process usually takes less than one second on a regular GPU. Recently, the use of DCNNs for image recovery and classification after transport through optical fibers has been reported. This combination opens new avenues for tremendous improvements of FOISs. For image transmission, two different types of optical fibers, MMF and glass-air Anderson localizing optical fiber (GALOF), have been utilized in recently reported DCNN-based FOISs. The DCNN-MMF based system is very sensitive to temperature variation and bending. In contrast, the DCNN-GALOF system demonstrated bending-independent imaging capabilities. This robust performance is based on the special mode properties of the GALOF. The modes embedded in the random structure of GALOF are formed by multiple scattering process. Each mode corresponds to a beam transmission channel. The imaging information is encoded and transferred by thousands of modes in the GALOF. Unlike MMF, most of these modes mediated by transverse Anderson localization demonstrate single-mode properties, which makes the device rather insensitive to external perturbations. The numerical simulation of the wave propagation process inside such structure requires huge computational power; therefore, combining the deep learning with GALOF is a preferable scheme.

Nevertheless, the aforementioned DCNN-GALOF fiber imaging system is faced with several challenges limiting its practical applications. Firstly, the system only demonstrated success in imaging simple objects such as MNIST handwritten numbers. There is a chasm between sparse objects reconstruction and the reconstruction of biological samples which are typically different types of cells or tissue with complicated morphologic features. In order to accomplish the demanding task to resolve and reconstruct the subtle details of biological samples, improved DCNNs which can "learn" the underlying physics of imaging process with higher precision are required. Secondly, the demonstrated transfer-learning capability of the previous DCNN-GALOF system was with binary sparse testing objects that were similar to training data. It would be more advantageous if the system could feature transfer learning performed using objects with features very different from the training data. Thirdly, the illumination of the previous DCNN-GALOF system relies on high-intensity, coherent laser light sources. The coherence of lasers results in speckle patterns that reduce the image quality. In addition, the high intensity of laser light might be damaging to biological objects such as living cells and the cost of lasers is relatively high. Compared to laser light sources, incoherent illumination, such as LED illumination, can generally give better imaging quality without speckle patterns. The low intensity of incoherent light also helps protect cells against photobleaching and phototoxicity during the imaging process. At the same time, the cost of LEDs is much lower compared to laser sources. Moreover, some medical practitioners might prefer incoherent light illumination. For example, white-light transmission cellular micrographs are already very familiar to histopathologists. Therefore, to develop a system using incoherent illumination is an important step towards practical applications.

The inventors have recognized the advantages and benefits of a novel imaging system that can deliver artifact-free images of biological objects using incoherent light while featuring the flexibility of optical fibers and lensless imaging of objects several millimeters away from the fiber facet. Such apparatus and methods are enabled as described herein below and in the appended claims.

SUMMARY

An embodiment of the invention is an optical imaging system. In an exemplary aspect the optical imaging system includes a length of a disordered transverse Anderson localizing fiber ('Anderson fiber') having a lensless distal end and a proximal end, and an object illumination channel between the proximal and distal ends; and a neural network having an input operationally coupled to the proximal end of the Anderson fiber to receive an input image of an object transmitted through the Anderson fiber and an output, wherein the neural network is configured to perform an image reconstruction process on the input image to generate an output image that is a high fidelity image of the object. In various non-limiting, exemplary embodiments and aspects the optical imaging system may exhibit one or more of the following features, characteristics, limitations, or functions alone or in various combinations:

- further comprising an object illumination channel between the proximal and distal ends;
- wherein the length of the disordered transverse Anderson localizing fiber is between 2 cm and 3 m;
- wherein the neural network is configured to provide an object classification after performing the image reconstruction process;
- wherein the object is illuminated by a narrowband coherent laser source with a wavelength between 350 nm and 2100 nm;
- wherein the object is illuminated by an incoherent light source with a center wavelength between 350 nm and 2100 nm and an emission linewidth between 1 nm and 50 nm;
  - wherein the incoherent light source is a light emitting diode.

An embodied imaging system can deliver artifact-free images of biological objects while featuring the flexibility of optical fibers and lensless imaging of objects several millimeters away from the fiber facet. The unique system performance can be achieved by combining image reconstruction using a trained deep neural network with low-loss image transmission through disordered glass-air Anderson localized optical fiber. The system provides a unique property that the training performed within a straight fiber setup can be utilized for high fidelity reconstruction for either straight or bent fiber, making retraining for different bending situations unnecessary. In addition, network retraining is not required if environmental changes occur, e.g., imaging at elevated temperatures. High quality image transport and reconstruction is demonstrated for cells that are several millimeters away from the fiber input facet eliminating the need for additional optical elements at the distal end of the fiber.

A non-limiting, exemplary embodiment is a DCNN-GALOF imaging system that uses incoherent light to illuminate the objects and has the capability to image various cell structures. Within this system, a new DCNN model with a tailored design is applied to the image reconstruction process, and a low-cost LED works as the light source. The system may be referred to herein as Cell-DCNN-GALOF. The system is able to provide high quality, artifact-free images of different types of cells in real time. The imaging depth of this system can reach up to several millimeters without any distal optics. In addition, the image reconstruction process is advantageously robust with regard to external perturbations, such as temperature variation and fiber bending. The embodied invention introduces a new platform for various practical applications such as neuroscience research and clinical diagnosis. It is also a new cornerstone for imaging research based on waveguide devices using transverse Anderson localization.

BRIEF DESCRIPTION OF THE DRAWINGS

FIG. 6a illustrates the detailed structure of the DCNN. FIG. 6b shows detailed block operation diagrams corresponding to the respective arrows shown on the left side (BN: Batch Normalization, ReLU: Rectified Linear Unit, Conv: Convolution, D-Conv: Dilated Convolution, T-Conv: Transposed Convolution, Concat: Concatenation), according to illustrative embodiments of the invention.

DETAILED DESCRIPTION OF NON-LIMITING, EXEMPLARY EMBODIMENTS

Figure 1:
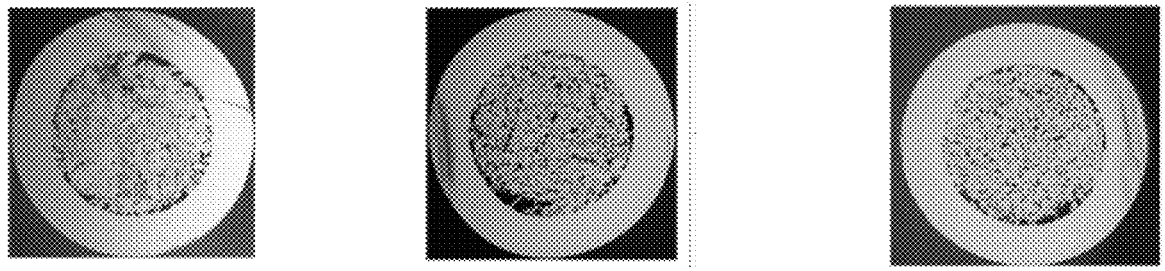
FIG. 1 shows cross sections of optical fibers with random glass-air dielectric structures fabricated at CREOL, according to an illustrative aspect of the invention.

Disclosed embodiments are described with reference to the attached figures, wherein like reference numerals are used throughout the figures to designate similar or equivalent elements. The figures are not drawn to scale and they are provided merely to illustrate aspects disclosed herein. Several disclosed aspects are described below with reference to example applications for illustration. It should be understood that numerous specific details, relationships and methods are set forth to provide a more complete understanding of the embodiments disclosed herein.

Transverse Anderson Localization in Glass Air Disordered Fiber

Highly multimode and multi-core optical fibers have successfully been used for transportation of images in various configurations. The most commonly used imaging fiber in scientific, medical, and industrial applications is multi-core fiber (MCF), which is often referred to as the "coherent fiber bundle." In a multi-core imaging fiber, a higher density of pixels (cores) results in a better image transport resolution. Conversely, maintaining a higher contrast favors distant cores, hence a lower pixel density, in order to minimize the crosstalk among cores. Therefore, there is an inherent conflict between the resolution and contrast of a transported image in a multi-core imaging fiber. Moreover, the images look highly pixelated. An imaging optical fiber that overcomes the resolution-contrast-pixelation issues while maintaining the robustness of the coherent fiber bundle is highly desired for all application fields.

Instead of using multimode or multi-core fibers for image transportation, we applied a novel type of disordered optical fibers that work on the principle of transverse Anderson localization (TAL) of light to the meet the challenge of high-quality image transportation. Anderson localization is the absence of diffusive wave transport in highly disordered scattering media. These fibers represent a completely new class of optical fibers that guide light, not in a conventional core/cladding setting, but by means of TAL, where many location sites across the transverse profile of the fiber are used to guide light. An optical beam can propagate along the disordered optical fiber while maintaining a finite beam cross-section due to the TAL effect caused by strong random scattering in the transverse plane.

Compared to polymer disordered fiber, glass-air Anderson localized optical fibers (GALOFs) have better performance in image transport due to lower loss of the glass materials and much smaller beam point spread functions. We recently demonstrated image transport through meter-long fiber. The transported images display a comparable or higher quality than the commercially available multi-core imaging optical fibers, with less pixelation and higher contrast. The resolution of the GALOF can be engineered through the refractive index contrast, glass-air volume ratio, the average feature size of the fiber, and the feature size distribution. It is also worth noting that that transverse Anderson localization is robust to bending. This inherent robustness is akin to the bend-insensitivity observed in ClearCurve fibers by Corning, where the presence of a random nanostructure results in an ultra-bendable fiber.

Advantageous features of the embodied GALOF imaging fiber are:
- At least part of the imaging fiber features a random refractive index structure in the fiber cross-section. This random structure is achieved through the mixing of two-four different dielectric materials. One of these materials can be air, while the other materials are different glasses.
- The average feature size within the random structure is between 0.1 and 10 times the wavelength that is applied for the imaging process. For visible light, e.g., this corresponds to average feature sizes from about 40 nm to about 7 μm.
- The refractive index structure remains approximately unchanged along the fiber axis.

Non-limiting, exemplary embodiments of the imaging fiber contain only two materials, air and silica glass. However, other oxide glasses including silicate, tellurite, and germanate glasses or non-oxide glasses such as chalcogenide or fluoride glasses can also be used. Furthermore, any mixture of these glasses can be used to create the random refractive index structure.

In non-limiting, exemplary embodiments of the imaging fiber the average feature sizes are approximately 1.6 µm, 3 µm, and 5 µm, all of which can be used to perform the imaging task at visible and near-IR wavelengths.

In non-limiting, exemplary embodiments the random refractive index structure is surrounded by a silica glass tube. This glass tube is not necessary. If used, the outer tube can have any outer diameter between approximately 50 µm and 1 mm. The outer tube can also be used to guide light from the proximal end of the fiber where the image is recorded to the distal end of the fiber in order to illuminate the object. Furthermore, additional light guiding structures can be integrated in the outer tube or into the random refractive index structure to perform the object illumination task.

In an exemplary method the GALOF is fabricated using the stack-and-draw method. Silica capillaries with different diameters and air-filling fractions are fabricated first. The outer diameter of the silica capillaries ranges from about 100 to 180 µm and the ratio of inner diameter to outer diameter ranges from 0.5 to 0.8. To make a preform, capillaries are randomly fed into a silica jacket tube. The preform is drawn to canes with an outer diameter around 3 mm. Finally, the cane is drawn to the GALOF with a desired size. FIG. 1. Shows cross sections of optical fibers with random glass-air dielectric structures fabricated at CREOL.

Machine Learning Based Image Reconstruction

An imaging system establishes a mapping from the object space to the measurement space of the imager. Isomorphic mapping, i.e., point-to-point mapping, has traditionally been desirable in imaging system design because the output is a direct duplicate of the original object. The computational imaging approach combines computational methods with non-isomorphic mapping and has shown great potential in relaxing the requirements of the imaging device.

A primary challenge of computational imaging systems is finding the inverse mapping algorithm. The inverse mapping algorithm is a set of procedures performed on the measurement, with the goal of inferring the image of the object. The measurement process can in some cases be mathematically modeled, such as in the cases of lens-based imaging, holography, and tomography systems. The inversion algorithms for such systems usually require accurate calibration of system parameters, and highly depend on the condition of the mathematical transform. In many cases including the embodied random fiber imaging system, the modeling and calibration of individual devices is prohibitively complicated.

Figure 2:
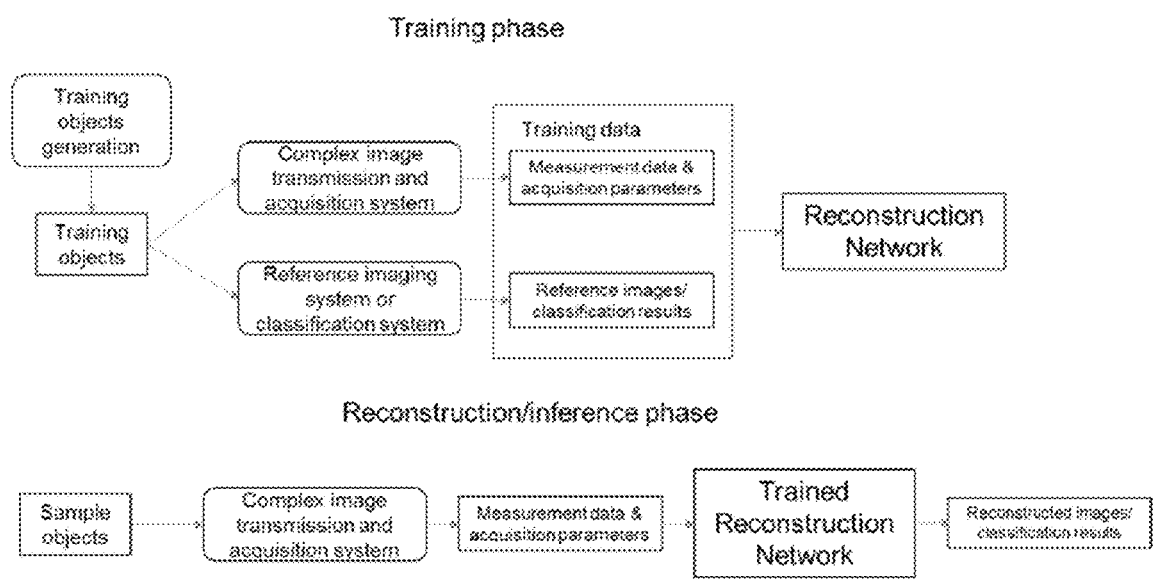
FIG. 2 shows a flow chart that illustrates the two phases of machine learning based reconstruction/classification: 1) A training phase, where the reconstruction network is optimized by a set of known training objects with known classification, and 2) A reconstruction/inference phase, where the images are reconstructed and/or the samples objects classified from the measurement of unknown samples by the trained reconstruction network, according to an illustrative aspect of the invention.

As such, a machine learning-based image reconstruction algorithm is adopted. As illustrated in FIG. 2, the machine learning based reconstruction includes two phases; 1) a training phase, where the reconstruction network is optimized by a set of known training samples; and 2) a reconstruction/inference phase, where the images are reconstructed from the measurement of unknown samples by the trained reconstruction network. The network can also be trained to classify the unknown samples.

During the training phase, a set of known objects are generated and placed at the imaging area. The training objects will be imaged by both the complex imaging system and a reference imaging system that provides high fidelity imaging capability of the sought-after property (e.g., irradiance, phase, coherence, polarization, etc.). The reference imaging system can be, for instance, a microscope or an optical coherence tomography device. The set training data for the reconstruction network consists of the measurements from the complex imaging system and the images from the reference image systems. Typically, datasets of several thousands of image pairs are used for the training phase.

Machine-Learning Based Random Fiber Imaging System for Biological Objects

The embodied fiber optical imaging system for biological objects combines disordered glass-air Anderson localized optical fiber (GALOF) for image transport with tailored computational methods for the reconstruction and classification of images of biological objects. It offers advantages in resolution, depth perception, bending robustness, and environmental stability over conventional fiber optic imaging methods.

Figure 3:
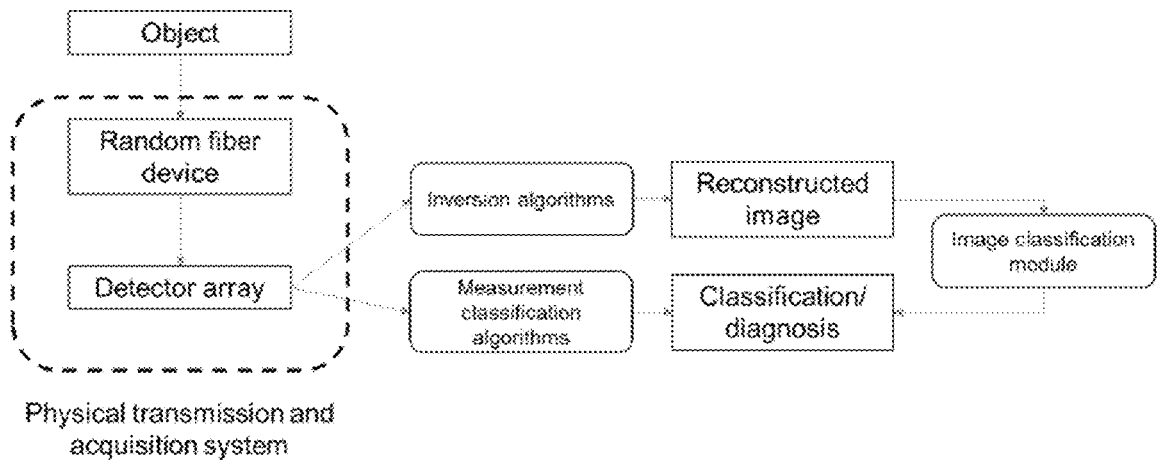
FIG. 3 is a schematic block diagram of a random fiber-based biological imaging system and method, according to an illustrative aspect of the invention.
Figure 4:
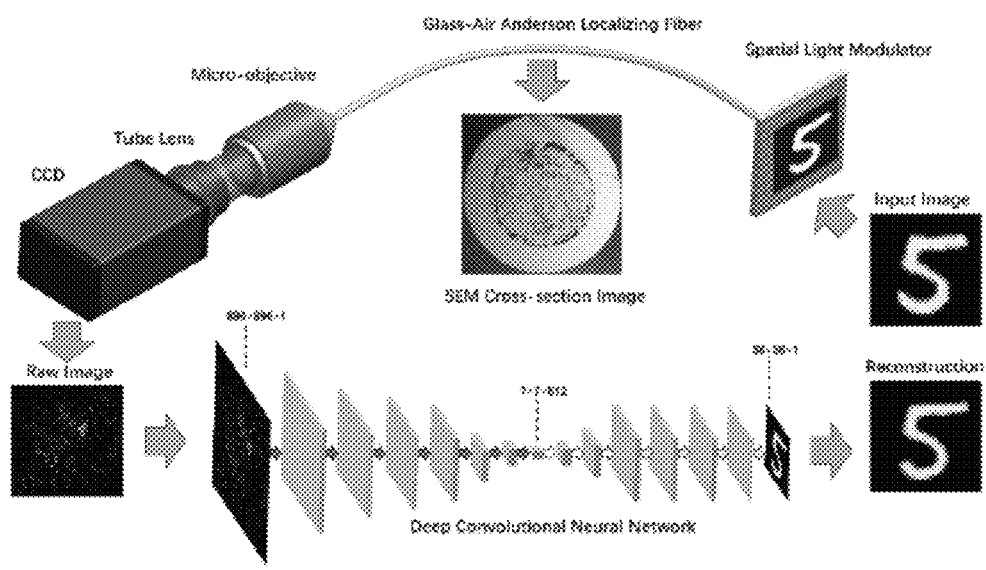
FIG. 4 schematically illustrates an experimental random fiber-based biological imaging system for the transmission and reconstruction of simple numbers, according to an illustrative aspect of the invention.

An aspect of the embodied method/apparatus is illustrated by the block diagram in FIG. 3. An early machine-learning based random fiber imaging system illustrated in FIG. 4 is composed of a physical image transmission and data acquisition system and associated reconstruction/classification algorithms. Light from the illuminated object of interest is transported by the random fiber device (GALOF) and collected by a detector array (typically a CCD camera). Depending on specific tasks, the measurement from the detector array can be processed by 1) an inversion algorithm for image reconstruction, or 2) a task-specific classification algorithm for classification or diagnosis. The reconstructed image can be further processed by an image classification module (human classification or other computer based classification algorithms). During the reconstruction/classification phase, only the GALOF fiber device is applied in image acquisition. Measurement data and the image acquisition condition are fed to the trained reconstruction network. The output of the network is the reconstructed images, which, for a functional and well-trained DNN, closely resemble the objects. In FIG. 4, simple numbers were used as very sparse objects.

Figure 5:
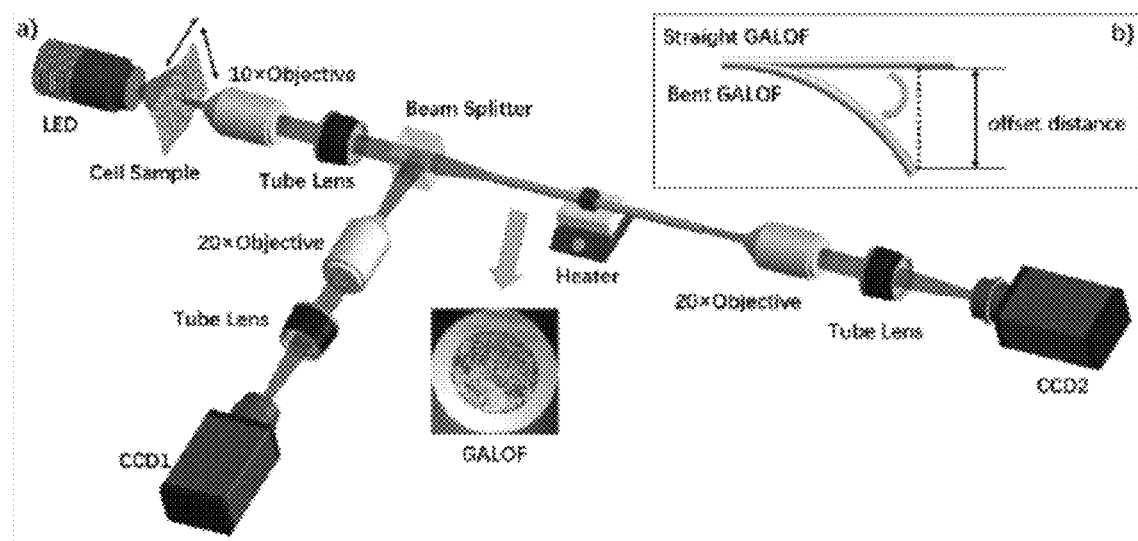
FIG. 5a schematically illustrates an experimental DCNN-GALOF imaging system using incoherent light-illumination of the objects with the capability to image various cell structures, according to an illustrative embodiment of the invention.
FIG. 5b: to quantify the amount of fiber bending the offset distance was measured, which is defined as the distance from the end of the bent fiber to the position of the straight fiber (equal to the length of the dashed line).
Figure 6:
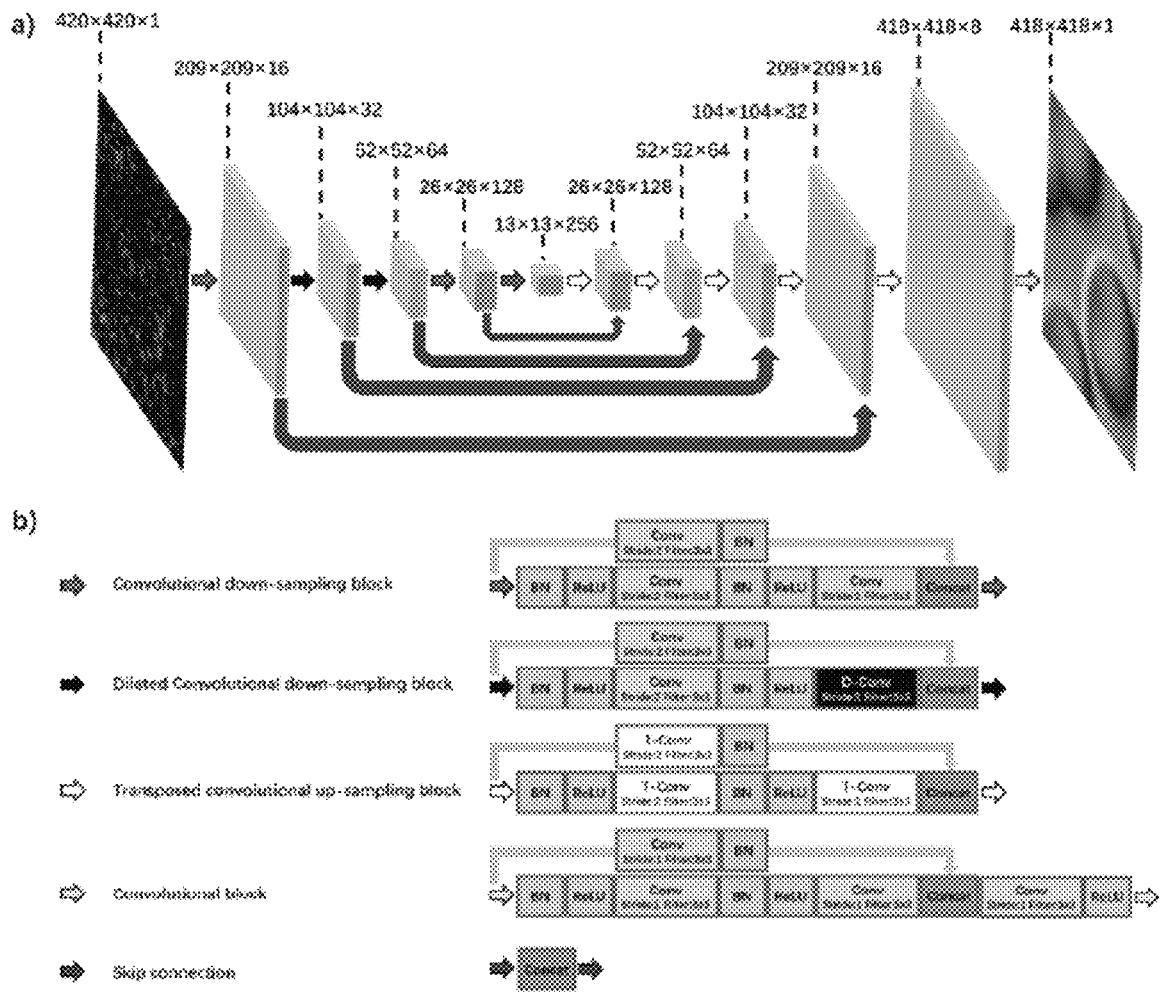
FIG. 6 schematically illustrates the architecture of the DCNN applied for reconstruction of various cell images shown in FIGS. 7-12.

FIGS. 5*a*, 5*b* schematically illustrate an experimental incoherent light-illuminated DCNN-GALOF imaging system, which notably has no distal optics, with the capability to image various cell structures. Within this system, a new deep convolution neural network (DCNN) model (see FIG. 6) is applied to the image reconstruction process, and a low-cost LED is employed as the light source. In FIG. 5*a*, the light source is a LED with a center wavelength of 460 nm. An 80 cm long GALOF sample is utilized. The SEM image of the GALOF cross-section is shown in the inset. The diameter of the disordered structure is about 278 µm, and the air-hole-filling fraction in the disordered structure is approximately 28.5%. The temperature of a GALOF segment can be increased by the heater underneath. The images of cell samples are magnified by a 10× objective and split into two copies that are sent into a reference path and a measurement path, respectively. The cell samples are scanned both vertically and horizontally with 5 µm steps to obtain training, validation, and test datasets. In the reference beam path, the image is further magnified by a 20× objective and recorded by CCD 1 (Manta G-145B) after passing through a tube lens. In the measurement path, the image is transported through the 80 cm long GALOF and then projected onto CCD 2 (Manta G-145B) by the same combination of 20× objective and tube lens. Experiments were performed for both straight GALOF and bent GALOF. To quantify the amount of bending, the offset distance was measured, which is defined as the distance from the end of the bent fiber to the position of the straight fiber (equal to the length of the dashed line) as shown in FIG. 5*b*.

Figure 7:
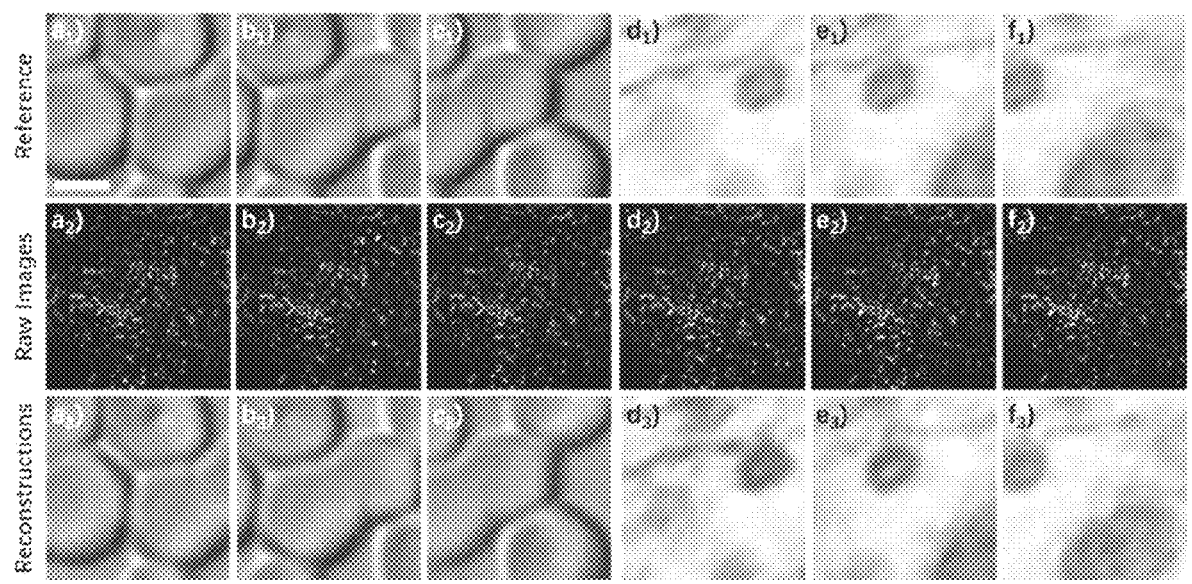
FIGS. 7($a_{1-3}$-$f_{1-3}$) show cell images of different types of cells. (a-c) are test data for human red blood cells; (d-f) are test data for cancerous human stomach cells. All data are collected with straight GALOF at room temperature with 0 mm imaging depth. The length of the scale bar in $a_1$ is 4 µm. $a_1$-$f_1$ are the reference images; $a_2$-$f_2$ are the corresponding raw images; $a_3$-$f_3$ are the images recovered from the raw images, according to an illustrative aspect of the invention.

Both reference and raw images are 8-bit grayscale images and are cropped to a size of 418×418 pixels. To demonstrate the imaging reconstruction capability, two different types of cells, human red blood cells and cancerous human stomach cells, serve as objects. By scanning across different areas of the cell sample we collected 15000 reference and raw images as the training set, 1000 image pairs as the validation set, and another 1000 image pairs as the test set for each type of cells. During the first data acquisition process, the GALOF was kept straight and at room temperature of about 20° C. The imaging depth is 0 mm, meaning that the image plane is located directly at the fiber input facet. The training data are loaded into the DCNN (see FIG. 6 for DCNN structure) to optimize the parameters of the neural network and generate a computational architecture that can accurately map the fiber-transported images to the corresponding original object. After the training process, the test data are applied to the trained model to perform imaging reconstruction and evaluate its performance using the normalized mean absolute error (MAE) as the metric as discussed further herein below. In the first round of experiments, we trained and tested each type of cell separately. With a training data set of 15000 image pairs, it takes about 6.4 hour to train the DCCN over 80 epochs on two GPUs (GeForce GTX 1080 Ti) using a personal computer. After training, the reconstruction time of a single test image is about 0.05 second. FIGS. 7($a_{1-3}$-$f_{1-3}$) show some samples from the test data set. In $a_{1-3}$-$c_{1-3}$ reference images, raw images, and recovered images of three in succession collected and reconstructed images of human red cells are shown, while in $d_{1-3}$-$f_{1-3}$ three images of cancerous stomach cells are presented. Comparing the reference images with the reconstructed images, it is clear that the separately trained DCNNs are able to reconstruct images of both cell types remarkably well. The averaged normalized test MAEs are 0.024 and 0.027 for the human red blood cells and the cancerous human stomach cells, respectively, with standard deviations of 0.006 and 0.011. To further highlight the real-time imaging capability of our system, we visualized the test process for these two cell types in a video; this real-time imaging capability is highly desirable for many practical applications such as in situ morphologic examination of living tissues in their native context for pathology.

Figure 8:
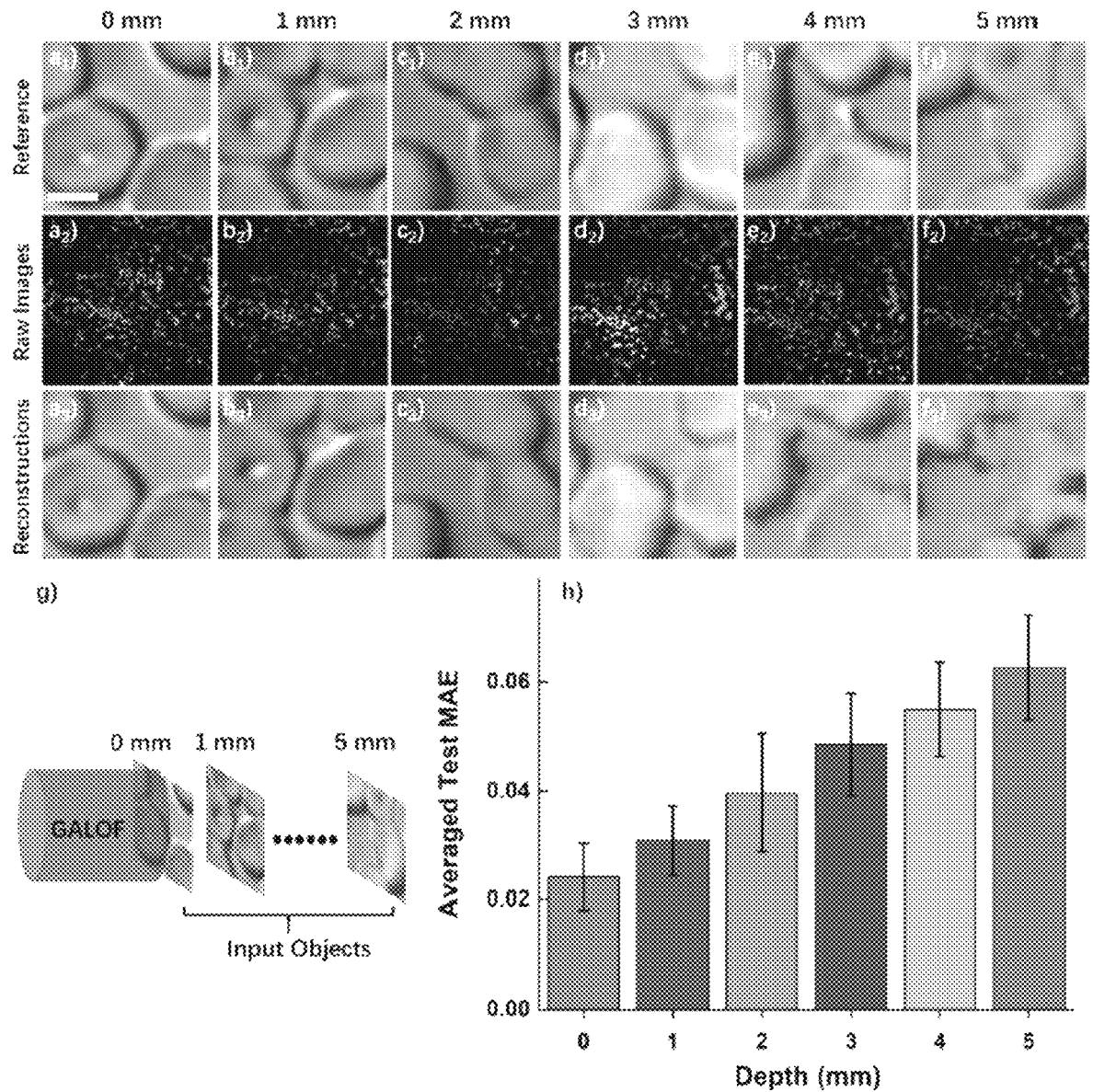
FIG. 8: Multiple depth cell imaging. a-f are test data for human red blood cells. All data are collected with straight GAFOF at room temperature. All three images in each column are from the same depth. The length of the scale bar in $a_1$ is 4 μm. $a_1$-$f_1$ are the reference images; $a_2$-$f_2$ are the corresponding raw images. As illustrated in g, $a_2$-$f_2$ are obtained by varying the imaging depth from 0 mm to 5 mm with steps of 1 mm. $a_3$-$f_3$ are the images recovered from the corresponding raw images. h is the averaged test MAE error for each depth with the standard deviation as the error bar.

The presence of distal optics located at the fiber input end hinders conventional FOIS from miniaturizing the size of the imaging unit. The embodied Cell-DCNN-GALOF apparatus and method enable the ability to image objects located at various distances from the fiber input facet without distal optics. As illustrated in FIG. 8g, the images of cells located at different imaging planes are collected by the bare fiber input end. The depth ranges from 0 mm to 5 mm with steps of 1 mm. For each individual depth, 15000 reference and raw images are collected as the training set, and another 1000 image pairs serve as the test set. The GALOF is kept straight and at room temperature during data collection. The DCNN is trained separately for each depth resulting in depth-specific parameters. Examining reference and reconstructed test images shown in FIGS. 8a-f, high-quality image transmission and reconstruction can be achieved up to depths of at least 3 mm. The first visual degradation of the imaging quality appears around 4 mm and the visual quality of the reconstructed images drops further at 5 mm depth. The corresponding quantitative image quality evaluation is shown in FIG. 8h. The normalized MAE increases almost linearly with a slope of about 0.008 per mm. Based on these data we conclude that our system can transfer high-quality cell images for objects being several mm away from the fiber input facet without the need for any distal optics. Therefore, the size of an image transmitting endoscope based on our system could be potentially minimized to the diameter of the fiber itself and the penetration damage could be reduced to a minimum without degrading the quality of the image of biological objects. The fiber could collect images of organs without touching them directly, enabling a minimally invasive, high performance imaging system.

FIG. 6a shows the architecture of an exemplary DCNN. The raw image which is resized to 420×420 pixels using zero padding is the input layer. The input layer is decimated by five down-sampling blocks (short arrows left of center) to extract the feature maps. Then five up-sampling blocks (short arrows right of center) and one convolutional block (right-most short arrow) are applied to reconstruct the images of cell samples with a size of 418×418 pixels. The skip connections (long bridge arrows) pass feature information from feature-extraction layers to reconstruction layers by concatenation operations. The MAE-based loss metrics are calculated by comparing the reconstructed images with the reference images. The parameters of the DCNN are optimized by minimizing the loss.

FIG. 6b shows detailed block operation diagrams corresponding to the respective arrows shown on the right side (BN: Batch Normalization, ReLU: Rectified Linear Unit, Conv: Convolution, D-Conv: Dilated Convolution, T-Conv: Transposed Convolution, Concat: Concatenation).

Loss Function

Mean squared error (MSE) and mean absolute error (MAE) are the most frequently used loss functions for deep convolutional neural networks (DCNNs). The loss function is a mathematical method to measure the difference between the deep-learning model output and the dataset. A higher value of the loss function indicates that the prediction of the deep-learning model deviates from truth. If the output of the model matches the data well, the loss function should be of a low value. An exemplary embodied method uses MAE as the loss function in all embodied DCNN models since it results in a better performance. In the recently published paper "Imaging through glass diffusers using densely connected convolutional networks, Vol. 5 No. 7 Optica 2018," another metric, the negative Pearson correlation coefficient (NPCC), was applied as the DCNN loss function.

Assume A(i,j) is the output of deep-learning model, B(i,j) is the ground truth, A and B are the mean values of A(i,j) and B(i,j), respectively; w and b are the height and width of the image. The definition of MSE, MAE and NPCC follow as:

$$MSE = \frac{1}{wb} \sum_{i=1}^{w} \sum_{j=1}^{b} (A(i,j) - B(i,j))^2 \quad (1)$$

$$MAE = \frac{1}{wb} \sum_{i=1}^{w} \sum_{j=1}^{b} |A(i,j) - B(i,j)| \quad (2)$$

$$NPCC = \frac{-1 \times \sum_{i=1}^{w} \sum_{j=1}^{b} (A(i,j) - \overline{A})(B(i,j) - \overline{B})}{\sqrt{\sum_{i=1}^{w} \sum_{j=1}^{b} (A(i,j) - \overline{A})^2} \sqrt{\sum_{i=1}^{w} \sum_{j=1}^{b} (B(i,j) - \overline{B})^2}} \quad (3)$$

Optimizer

During the training phase of the DCNN, the parameters of the DCNN model are changed to minimize the loss function. The specific mathematical method to update the parameters are called optimizers. The loss function value tells the optimizer the right direction in the training process. People have developed several different algorithms to optimize deep learning models. We use the Adam optimizer since it is a frequently used and very effective optimizer. There are other possible choices for optimizer: SGD optimizer, RMSProp optimizer, Adagrad Optimizer, Adadelta optimizer, Adamax optimizer, Nadam optimizer.

Regularization, L1 and L2 Norm

Regularization is a term added into the loss function to penalize certain parameters and avoid overfitting. Overfitting means the deep-learning model fits well on the limited training data but cannot predict well on test data. Overfitting happens when the parameter is weighted too heavily and ends up dominating the formula. Take a simple linear regression problem as an example. Assume the machine learning model is $h_\theta(x) = \theta_0 x_1 + \theta_1 x_2 + \theta_2 x_3 \ldots \theta_n x_n$, the corresponding reference dataset is $(y_1, y_2, y_3, \ldots, y_n)$, $\lambda$ is a parameter which can be tuned, then the loss function with a regularization term can be written as:

$$L(\theta) = \frac{1}{2m}\left[\sum_{i=1}^{n}(h_\theta(x_i) - y_i)^2 + \lambda\sum_{j=1}^{m}\theta_j^2\right] \quad (4)$$

or:

$$L(\theta) = \frac{1}{2m}\left[\sum_{i=1}^{n}(h_\theta(x_i) - y_i)^2 + \lambda\sum_{j=1}^{m}|\theta_j|\right] \quad (5)$$

The term $\lambda\sum_{j=1}^{m}\theta_j^2$ or $\lambda\sum_{j=1}^{m}|\theta_j|$, is the regularization term. When it is in the absolute value form (5), it is called a L1-norm. When the squared value is used (4), it is called a L2-norm. In our model, we use the L2-norm. In our cell imaging problem, using the L2-norm results in better performance than using the L1-norm. That does not mean that the L1-norm cannot be used in our or other problems; we select the better performance for our specific research problem.

Initialization

We initialize our DCNN model using Glorot normal initialization. There are some other choices including Glorot uniform initialization, He normal initialization, He uniform initialization, LeCun normal initialization, and LeCun uniform initialization, to name but a few. For our specific problem using a normal distribution initialization works better than applying a uniform distribution initializer.

Both the ACS model and the NC model can be called residual convolutional neural networks, because we use skip connections either between layers (NC model) or inside the single blocks (units) (ACS model) indicated by the arrows inside the areas marked by red-dashed lines. These skip connections significantly improve the performance of the deep convolutional neural networks.

It appears that the green skip connections between layers in the NC model (1) are not necessary for relatively simple tasks, just like in the ACS model (1). From our experience, the ACS model (1) can even handle some cell imaging with simple-structure cells, such as red blood cells. But for cells with more complex fine structures, such as stomach cells, the AP model (1) does not work well.

In the ACS model (2), two matrices are added directly at the output of the skip connections. In NC model (2), two matrices are concatenated to form a larger matrix. This concatenation is found to be very important for improving the DCNN's performance in recovering cells with complex fine structures.

In both the ACS model and the NC model, inside the units (blocks), the sequence of each operation is BN→ →Relu →Conv. In fact, this sequence is not that critical; it could be rearranged as Conv→ BN →Relu.

The NC model includes dilated convolutional down-sampling blocks which cannot be found in ACS model. These additional blocks improve the cell imaging performance and turn out to be more important than the sequence of BN, Relu, and Conv.

In all of our deep learning models we use the filter size 3×3. This can be changed to either 5×5 or 7×7, there is no strict rule. We use 3×3 filters because we followed other papers applying similar DCNNs to perform imaging reconstruction.

ReLu is a nonlinear activation function to introduce nonlinearity into the learning model. We use ReLu because it is empirically found to be very effective in the computer science community. But there are also other activation functions in machine learning models which might also be used here, for instance, the Sigmoid activation function and the Tan h activation function.

Cell Imaging with Temperature Variation and Fiber Bending

In practical applications, the optical fiber of the FOIS often needs to be inserted deeply into the cavity of living organs. This requires the imaging system to tolerate thermal variation and fiber bending. For MMF-based FOIS, the increase of temperature or bending of the fiber when inserting fiber into organs or tissues induces strong variations of the mode coupling. These variations decrease the performance of MMF-based imaging systems due to induced changes of the transmission matrix. This problem can be overcome by using GALOF since most of the modes embedded in GALOF show single mode characteristics, which increases the system tolerance and can make it immune even to rather strong perturbations. We first investigate the effect of temperature variation on our Cell-DCNN-GALOF system by changing the temperature of a 10 mm long GALOF segment with a heater. During the data collection, we keep the GALOF straight and at 0 mm imaging depth. We collect 15000 image pairs at 20° C. as the training data. For test data, we record three sets of test data where the GALOF segment is heated to 20° C., 35° C., and 50° C., respectively (see FIG. 5). Each set of test data consists of 1000 image pairs. The DCNN model is only trained utilizing the training data collected at 20° C. Subsequently, the trained model is applied to perform test image reconstruction of data acquired at all three different temperatures.

Figure 9:
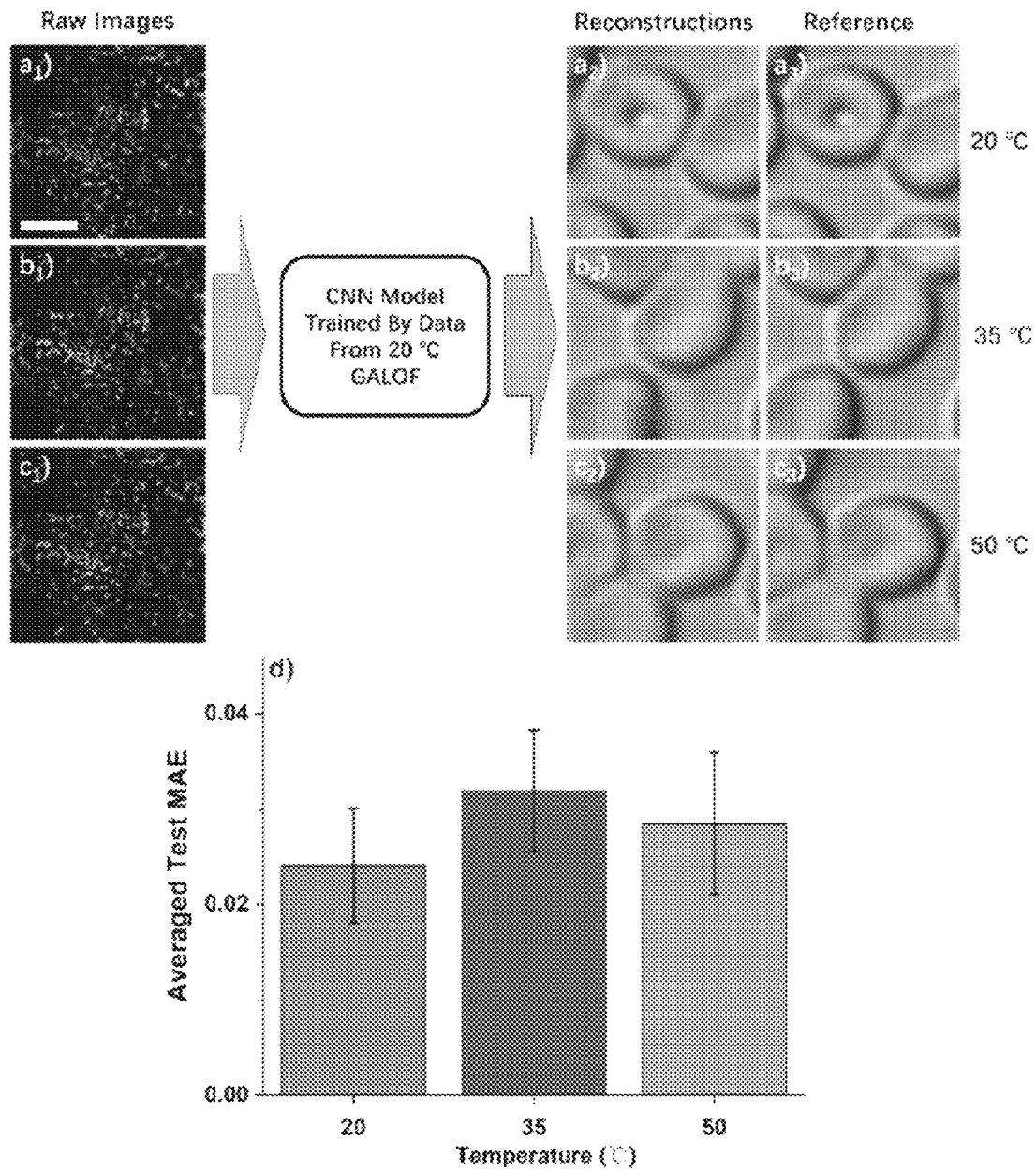
FIG. 9: Cell imaging at different temperatures. $a_1$-$c_1$ are test raw images of human red blood cells collected with the heater (see FIG. 5a) set to 20° C., 35° C., and 50° C., respectively. The length of the scale bar in $a_1$ is 4 μm. $a_2$-$c_2$ are the images recovered from $a_3$-$c_3$ are the corresponding reference images. All data are collected with straight GALOF at 0 mm imaging depth. d shows the test MAE (mean average error) averaged over 400 test objects for each temperature with the standard deviation as the error bar.

In FIGS. 9a-c some sample images are shown. Comparing the reference with reconstructed images, the visual imaging quality is not affected by a temperature change of 30° C., which confirms the remarkable robustness of the embodied Cell-DCNN-GALOF system regarding temperature fluctuations, which makes the system particularly suitable for in vivo imaging.

Figure 10:
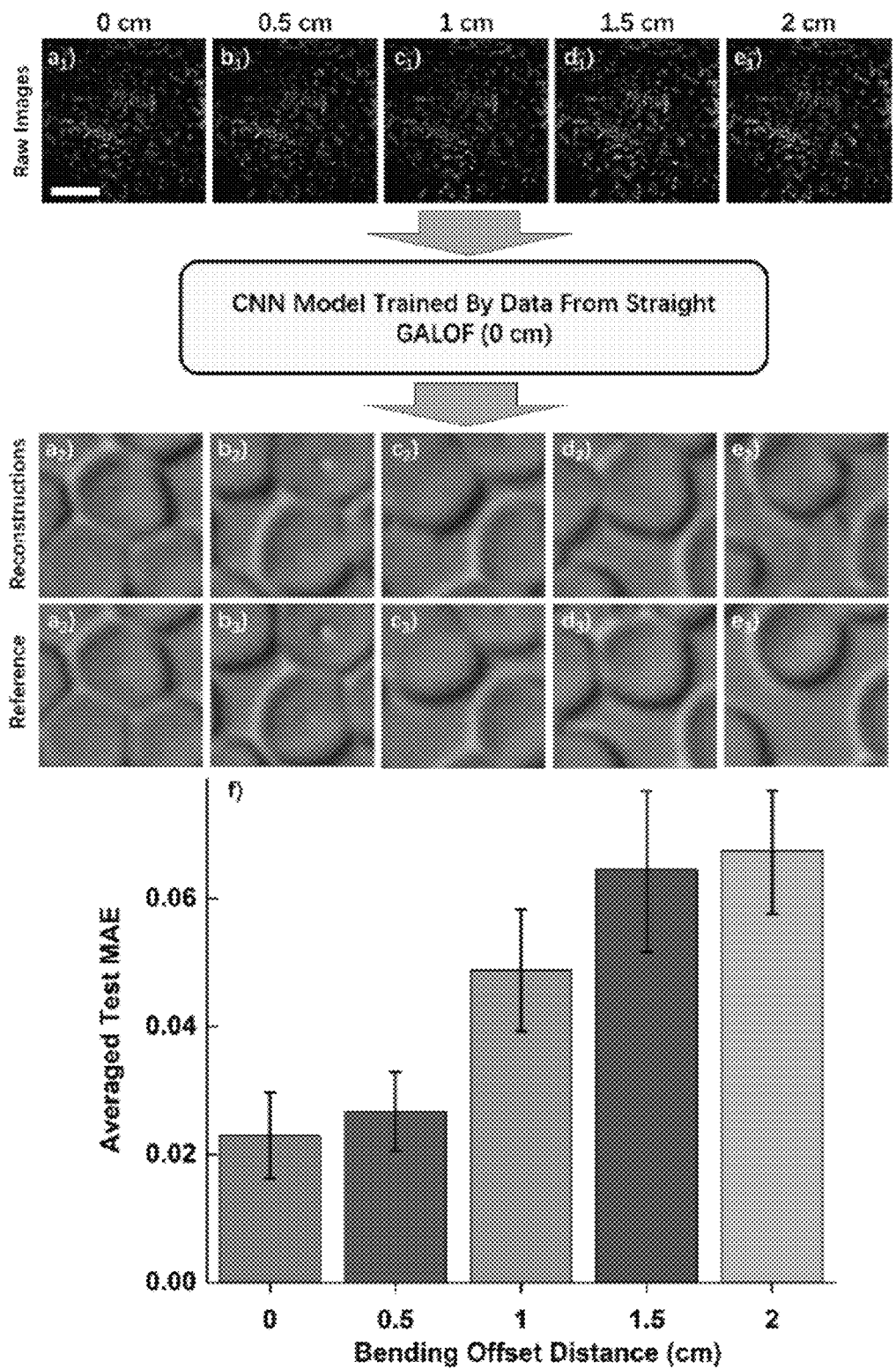
FIG. 10: Cell imaging under bending. Data in each column a-e correspond to examples with the bending offset distance listed above. The definition of offset distance is illustrated in FIG. 5b. The bending angle range corresponding to offset distances between 0 cm and 2 cm is about 3 degrees. $a_1$-$e_1$ are raw images collected at different bending offset distances. The length of the scale bar in $a_1$ is 4 μm. $a_2$-$e_2$ are the images reconstructed from $a_1$-$e_1$. $a_3$-$e_3$ are the corresponding reference images. f shows the averaged test MAE for five different bending states with the standard deviation as the error bar.

Next, we test the effect of fiber bending on the performance of our Cell-DCNN-GALOF system. We keep the temperature of the fiber at room temperature and the imaging depth at 0 mm. We collect 15000 image pairs with straight GALOF as the training data and record five sets of separate test data corresponding to five different bending states. Each test set consists of 1000 image pairs. Experimentally, the bending is induced by moving the fiber end by a specified offset distance as illustrated in FIG. 5b. We first train the model only using the training data collected from straight GALOF. Then test images from all five different bending states are reconstructed by the non-bending-data trained DCNN model and evaluated using the MAE. The results are shown in FIG. 10. Based on the recovered images in FIGS. 10$a_2$ to $e_2$, high fidelity cell imaging transfer and reconstruction could be performed without any retraining for offset distances smaller than 2 cm (a bending angle of ~3 degrees). The corresponding change of the normalized averaged MAE with bending is depicted in FIG. 10$f$. Within this small bending limit every degree of bending results in a MAE increase of about 0.02. This is in sharp contrast to MMF-based systems which require access the distal end of the fiber to recalibrate the transmission matrix if any tiny movement (a few hundred micrometers) of the MMF happens. For neuroscience applications the flexibility of the Cell-DCNN-GALOF system shows the potential to satisfy the imaging requirements for observing real-time neuron activity in free-behaving objects.

Cell Imaging Transfer Learning

Figure 11:
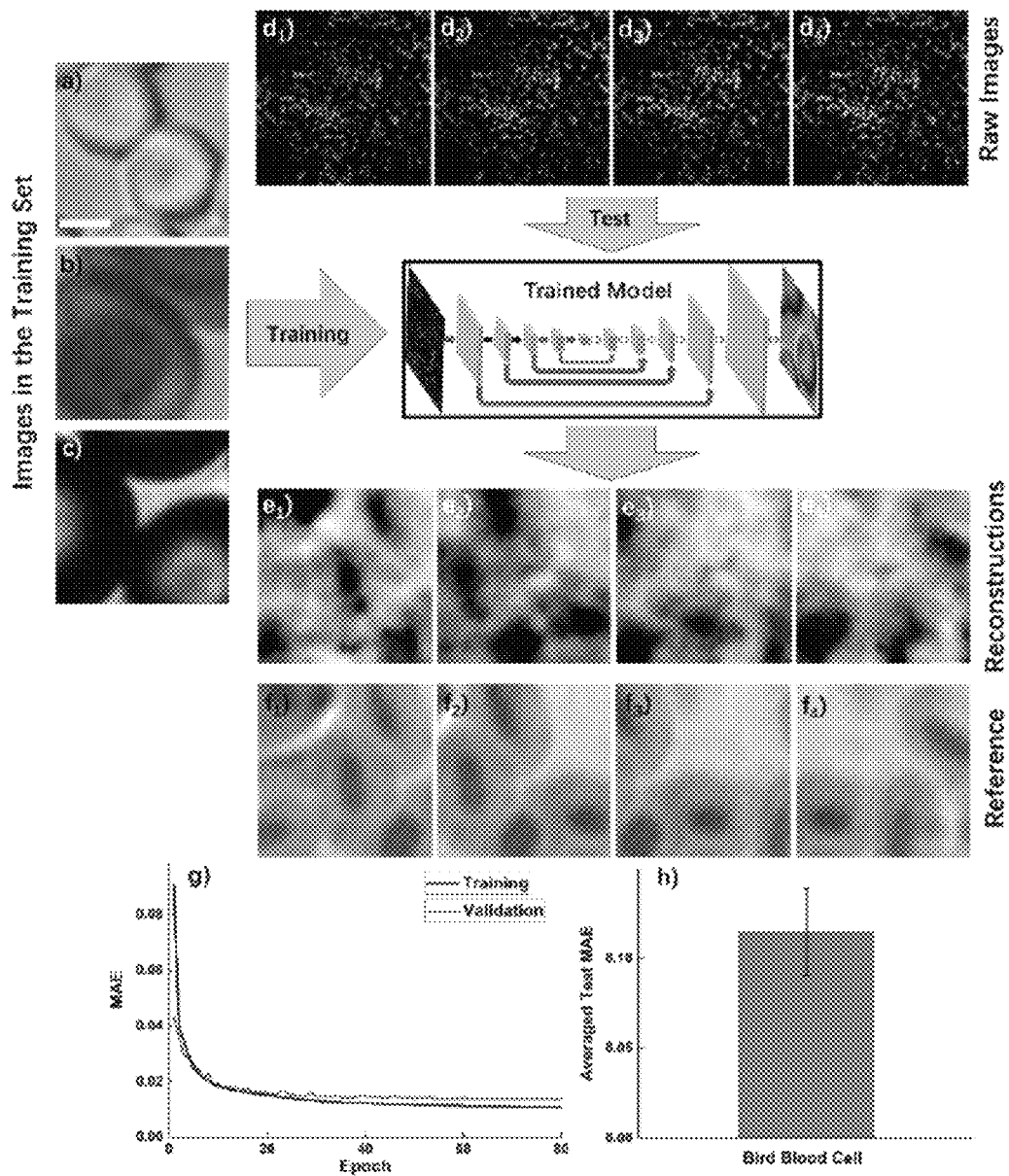
FIG. 11: Cell imaging transfer learning. a-c are sample cell images in the set of training data. The length of the scale bar in a is 4 μm. There are three different types of cells in the set of training data; a) is an image of human red blood cells, b) is an image of frog blood cells and c) is an image of polymer microspheres; d-f demonstrate the test process using data from images of bird blood cells. $d_1$-$d_4$ are the raw images of bird blood cells transported through straight GALOF taken at 0 mm imaging depth and at room temperature. $e_1$-$e_4$ are images reconstructed from $d_1$-$d_4$. $f_1$-$f_4$ are the corresponding reference images of bird blood cells. g) The training and validation accuracy improvement curves using MAE as the metric over 80 epochs. h) shows the averaged test MAE of the bird blood cells images with the standard deviation as the error bar.
Figure 12:
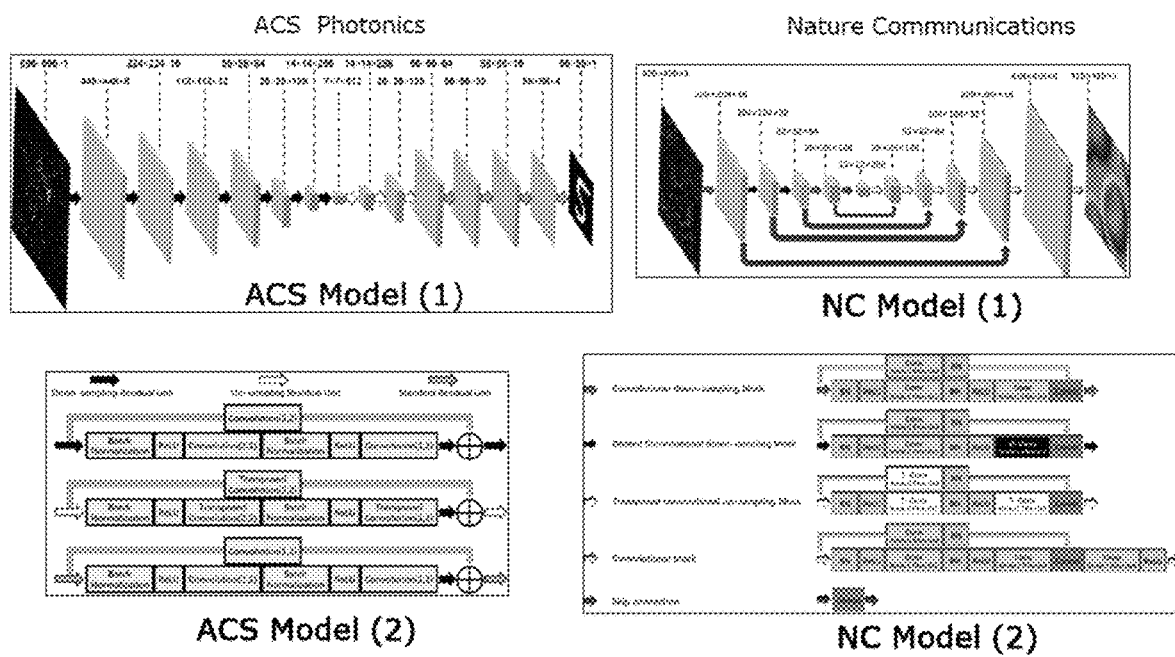
FIG. 12 shows the architectures of two DCNNs comparing a simpler DCNN for the reconstruction of numbers and letters (ACS model, left hand side) with the more complex DCNN for the reconstruction of the cell images (NC model, right hand side, see also FIG. 6).

We have shown that our DCNN is able to perform high-fidelity image restoration when training and testing is performed with the same types of cells. In practical applications, the Cell-DCNN-GALOF system would be a more efficient and higher functionalized tool if it was able to transfer its learning capability to reconstruct different types of cells which never appeared in the set of training data. To enable transfer-learning reconstruction with high fidelity, a training dataset with high diversity would certainly be beneficial. As a proof-of-concept experiment, we apply a training set with just three different types of images. Sample images are shown in FIGS. 11$a$-$c$. These are images of human red blood cells, frog blood cells, and polymer microspheres. During the recording of data for training, validation, and testing we keep the GALOF straight, the imaging plane at 0 mm depth, and at room temperature. To generate data sets for training and validation, we first collect 10,000 image pairs of each human red blood cells, frog blood cells, and polymer microspheres. Subsequently, all 30,000 image pairs of three different types are mixed randomly. We extract 28,000 image pairs from those randomly mixed images as the training dataset and 1000 image pairs as the validation dataset. To characterize the training process, the accuracy improvement curves during training and validation are tracked and shown in FIG. 11$g$. Both curves show convergence to low values after about 20 epochs. The differences between the validation and the training accuracy improvement curves are very small. These characteristics indicate that our DCNN is not overfitting with respect to the training dataset.

As the test data, we record 1000 image pairs from a totally different type of cells, namely bird blood cells. The raw images of the bird blood cells obtained after passing through straight GALOF are shown in FIG. 11$d$. These data are fed into the trained DCNN to perform the transfer-learning reconstruction. The reconstructed and reference images are shown in FIGS. 11$e$ and $f$, respectively. To enable a quantitative analysis, the averaged test MAE and its standard deviation are provided in FIG. 11$h$. A visual inspection demonstrates that within the reconstructed images of bird blood cells one can clearly locate the position and orientation of the nucleus for each single cell. Being trained by a fairly limited set of training data, our DCNN is still able to approximately reconstruct complex cell objects of a totally different type. This transfer-learning capability Cell-DCNN-GALOF system demonstrates that the underlying physics of the imaging process are captured well by the trained DCNN and should prove beneficial for practical applications.

We have developed a novel Cell-DCNN-GALOF imaging system and demonstrated its ability to provide artifact-free, high fidelity images of different types of cell in real time. Considering the complex morphology of various cells this represents a big leap forward compared to the reported capabilities of previous DCNN based FIOSs imaging systems.

Unlike conventional FOISs using distal optics, DCNN based systems feature the unique ability to image biological objects that are several millimeters away from the fiber facet without any distal optics. This is possible because the DCNN can be trained to accurately model the complete image transfer process including fiber transmission and free space propagation. Despite this advantage, the imaging quality of our Cell-DCNN-GALOF system gradually reduces with increasing imaging depth. This might be attributed to the fact that, under incoherent illumination, high-frequency features of the intensity objects are gradually lost with increasing imaging depth leading to a corresponding rise of the MAE.

Our Cell-DCNN-GALOF system is remarkably robust with respect to thermal and mechanical perturbations of the image transporting GALOF. This makes our system particularly suitable for in vivo biomedical imaging. This robustness is difficult to achieve with MMF-based system even with deep learning reconstruction algorithms. The displayed advantages in performance robustness are based on the different mode propagation properties of GALOFs leading to enhanced single mode guidance and reduced mode interference effects in GALOFs. However, it is worth noting that the imaging quality of the Cell-DCNN-GALOF system starts to degrade if the bending is larger than 3 degrees. This might be attributed to remaining multimode channels embedded in the random structure even if most transmission channels demonstrate single-mode properties. The path to improved bending independence will be a further optimization of the random structure inside the GALOF. It should be possible to maximize the scattering in the transverse plane, which would further enhance transverse light localization. Therefore, GALOF-based imaging system could potentially provide even stronger robustness through optimization of GALOF design and fabrication.

As a proof-of-concept we also show transfer-learning capabilities of our imaging system when images of different cell types that are not part of any training procedure can be reconstructed. We consider these experiments a proof of concept since we believe that a lot of improvement can be achieved in this area when suitable training data with larger diversity are applied. However, generating highly diverse biological training data for a FOIS remains a formidable practical challenge and the computational power available to process large amounts of training data is often an additional bottleneck. We believe that these challenges can be addressed in next generation FIOSs for biological objects with the help of further optimized DCNN architectures.

It is the combination of unique GALOF properties and tailored DCNN design that enables the remarkable capabilities of the presented Cell-DCNN-GALOF imaging system.

In the experiments of testing the imaging system tolerance with regard to thermal variations, a 10 mm-long section in the middle of the GALOF is heated. To bend the fiber, the input end of the GALOF is fixed while the output end of the GALOF is moved by an offset distance d. The relation between the offset distance and the corresponding bending angle of the fiber is given by $d=L[1-\cos(\theta)]/\theta$ where L is the total length of the GALOF.

The Keras framework was applied to develop the program code for the DCNN. The MAE is defined as $|I_{rec}-I_{ref}|/(wh)$, where $I_{rec}$, $I_{ref}$, w, and h are the reconstructed image intensity, the reference image intensity, the width, and the height of the images, respectively. The regularization applied in the DCNN is defined by the L2-norm. The parameters of the DCNN are initialized by a truncated normal distribution. For both training and evaluation, the MAE is utilized as the metric. The Adam optimizer is adopted to minimize the loss function. During the training process, the batch size is set at 64 and the training is run through 80 epochs with shuffling at each epoch for all the data shown in this paper. The learning rate is set at 0.005. Both training and test process are run in parallel on two GPUs.

While various disclosed embodiments have been described above, it should be understood that they have been presented by way of example only and not as a limitation. Numerous changes to the disclosed embodiments can be made in accordance with the specification herein without departing from the spirit or scope of this specification. Thus the breadth and scope of this specification should not be limited by any of the above-described embodiments; rather, the scope of this specification should be defined in accordance with the appended claims and their equivalents.

We claim:

1. A deep convolutional neural network glass-air Anderson localizing optical fiber (DCNN-GALOF) optical imaging system, comprising:
   an incoherent, continuous, broadband (non-monochromatic) object illumination source operationally coupled to an object illumination channel;
   an optical measurement path and an optical reference path optically coupled to the object illumination channel,
   a length of a disordered transverse Anderson localizing fiber ('Anderson fiber') having a lensless distal end and a proximal end disposed in the optical measurement path;
   an object illumination scanner disposed in the object illumination channel; and
   a deep convolutional neural network having an input operationally coupled to the proximal end of the Anderson fiber to receive an input image of an biological object, disposed in the object illumination channel, said image transmitted through the Anderson fiber and an output, wherein the neural network is configured to perform an image reconstruction process on the input biological image to generate an output image that is a high fidelity image of the biological object.

2. The optical imaging system of claim 1, wherein the length of the disordered transverse Anderson localizing fiber is between 2 cm and 3 m.

3. The optical imaging system of claim 1, wherein the neural network is configured to provide an object classification after performing the image reconstruction process.

4. The optical imaging system of claim 1, wherein the incoherent, continuous, broadband (non-monochromatic) object illumination source is a light emitting diode that emits light with a wavelength between 350 nm and 2100 nm.

5. The optical imaging system of claim 1, wherein the continuous, broadband (non-monochromatic) object illumination source is a white light source.

6. The optical imaging system of claim 1, wherein the light emitting diode (LED) object illumination source has a center wavelength of 460 nm.

7. The optical imaging system of claim 1, wherein the biological object is a cellular structure.

8. A deep convolutional neural network glass-air Anderson localizing optical fiber (DCNN-GALOF) method for imaging a biological object, comprising:
   providing a biological sample object;
   illuminating the biological sample object with continuous, incoherent light;
   scanning the biological sample object with the continuous, incoherent illumination over a plurality of vertical and horizontal positions to obtain training, validation, and test image datasets;
   obtaining an image dataset of the biological object at each position;
   splitting each image dataset into at least two copies;
   sending one image dataset copy into a reference optical path and recording said reference image with a reference recorder;
   transmitting another image dataset copy through a length of GALOF disposed in a measurement optical path and recording the GALOF output image with a measurement recorder;
   dividing a plurality of reference and measurement image datasets into the training, validation, and test image datasets;
   using the training and validation image datasets to train a deep learning convolutional neural network disposed in the system;
   record an image of a biological sample to be identified, transmit it through the GALOF, record it with the measurement recorder, and transmit it through the deep learning convolutional neural network; and
   recover a high-fidelity image of the new biological sample in real time.

9. The method of claim 8, comprising providing the continuous, incoherent light from a LED.

10. The method of claim 8, comprising providing the continuous, incoherent light from a white light source.

* * * * *